United States Patent
Goodin et al.

(10) Patent No.: US 7,488,304 B2
(45) Date of Patent: Feb. 10, 2009

(54) COVERED HYPOTUBE TO DISTAL PORT BOND

(75) Inventors: Richard L. Goodin, Blaine, MN (US); Victor L. Schoenle, Greenfield, MN (US); Daniel K. Tomaschko, Savage, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 662 days.

(21) Appl. No.: 10/266,979

(22) Filed: Oct. 8, 2002

(65) Prior Publication Data

US 2004/0068240 A1    Apr. 8, 2004

(51) Int. Cl.
*A61M 29/00* (2006.01)
*A61M 25/16* (2006.01)
*A61F 11/00* (2006.01)

(52) U.S. Cl. ............... 604/103.09; 604/535; 606/108

(58) Field of Classification Search ......... 606/108, 606/194; 604/103.09, 535
See application file for complete search history.

(56) References Cited

U.S. PATENT DOCUMENTS

| | | | |
|---|---|---|---|
| 4,251,305 A | 2/1981 | Becker et al. ............. 156/86 |
| 4,636,272 A | 1/1987 | Riggs ....................... 156/158 |
| 4,748,982 A | 6/1988 | Horzewski et al. ........ 128/344 |
| 4,943,278 A | 7/1990 | Euteneuer et al. .......... 604/96 |
| 4,964,409 A | 10/1990 | Tremulis ................... 128/657 |
| 5,047,045 A | 9/1991 | Arnery ...................... 606/194 |
| 5,100,381 A | 3/1992 | Burns ......................... 604/96 |
| 5,120,308 A | 6/1992 | Hess .......................... 604/95 |
| 5,154,725 A | 10/1992 | Leopold .................... 606/194 |
| 5,156,594 A | 10/1992 | Keith ......................... 604/96 |
| 5,279,562 A | 1/1994 | Sirhan et al. ............... 604/96 |
| 5,295,961 A | 3/1994 | Niederhauser et al. ...... 604/96 |
| 5,300,025 A * | 4/1994 | Wantink .............. 604/103.09 |
| 5,304,134 A | 4/1994 | Kraus et al. ................ 604/96 |
| 5,304,198 A | 4/1994 | Samson .................... 606/194 |
| 5,306,247 A | 4/1994 | Pfenninger ................. 604/96 |
| 5,334,187 A | 8/1994 | Fischell et al. ............ 604/194 |
| 5,346,505 A | 9/1994 | Leopid ..................... 606/194 |
| 5,370,616 A | 12/1994 | Keith et al. ............... 604/102 |
| 5,370,655 A | 12/1994 | Burns ....................... 606/194 |
| 5,387,193 A | 2/1995 | Miraki ....................... 604/96 |
| 5,395,334 A | 3/1995 | Keith et al. ............... 604/102 |
| 5,397,306 A | 3/1995 | Nobuyoshi et al. .......... 604/96 |
| 5,439,447 A | 8/1995 | Miraki ....................... 604/96 |
| 5,480,383 A | 1/1996 | Bagaoisan et al. .......... 604/96 |
| 5,522,818 A | 6/1996 | Keith et al. ............... 604/102 |
| 5,549,552 A | 8/1996 | Peters et al. ................ 604/96 |

(Continued)

*Primary Examiner*—(Jackie) Tan-Uyen T. Ho
*Assistant Examiner*—Melissa Ryckman
(74) *Attorney, Agent, or Firm*—Vidas, Arrett & Steinkraus

(57) ABSTRACT

A catheter assembly and method for constructing same comprises engagement of a proximal tubular member to a distal outer tubular member. At least a portion of the exterior surface of the proximal tubular member comprises at least one thermoplastic polymer. At least a portion of the end region of the distal outer tubular member is engaged to at least a portion of the end region of the proximal tubular member to define an engagement region. The proximal tubular member and the distal outer tubular member define a continuous central lumen therethrough. At least a portion of the proximal tubular member is disposed about an inner support layer. At least a portion of the inner support layer extends distally across the engagement region and into the lumen of the distal outer tubular member.

35 Claims, 6 Drawing Sheets

U.S. PATENT DOCUMENTS

| | | |
|---|---|---|
| 5,567,203 A | 10/1996 | Euteneuer et al. ............. 604/96 |
| 5,702,439 A | 12/1997 | Keith et al. ................... 604/96 |
| 5,980,484 A | 11/1999 | Ressemann et al. ........... 604/96 |
| 6,129,708 A | 10/2000 | Enger .................... 604/103.04 |
| 6,273,879 B1 | 8/2001 | Keith et al. ................. 604/523 |
| 6,319,229 B1 | 11/2001 | Kim et al. ................... 604/103 |
| 6,361,529 B1 | 3/2002 | Goodin et al. .............. 604/524 |
| 6,368,302 B1 | 4/2002 | Fitzmaurice et al. ... 604/103.04 |
| 6,461,347 B1 | 10/2002 | Von Hoffmann ............ 604/508 |
| 7,037,291 B2 * | 5/2006 | Lee et al. ............... 604/103.04 |
| 2001/0045257 A1 | 11/2001 | Pepin |
| 2002/0038103 A1 | 3/2002 | Estrada et al. |

* cited by examiner

COVERED HYPOTUBE TO DISTAL PORT BOND

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention is directed to a variety of embodiments. At least one embodiment of the invention is directed to the field of intravascular medical devices, and more particularly to the field of catheters such as angioplasty, neurological and guide catheters, among others, which may be used in various medical procedures such as percutaneous transluminal angioplasty (PTA), percutaneous transluminal coronary angioplasty (PTCA) as well as in procedures involving the placement of medicines and medical devices within the body.

Some embodiments of the invention are directed to all forms of catheters which may be advanced through a body lumen or vessel. Some examples of catheters are over-the-wire (OTW) catheters, such as are described in U.S. Pat. No. 5,047,045; single-operator-exchange (SOE) balloon catheters, such as are described in U.S. Pat. Nos. 5,156,594 and 5,549,552. Other examples of catheters which may incorporate the unique features of the present invention include monorail/rapid-exchange style balloon catheters, etc.

2. Description of the Related Art

Intravascular diseases are commonly treated by relatively non-invasive techniques such as PTA and PTCA. These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened. In other uses a catheter may be used to deliver an endoprosthesis such as a stent, graft, stent-graft, vena cava filter or other implantable device or devices herein after collectively referred to as a stent or stents. Where a stent is to be delivered into a body lumen the catheter may include one or more inflatable portions or balloons. Typically, the stent is retained in the predelivery state about the catheter shaft, or a portion thereof such as a balloon, by crimping and/or through the use of a retaining mechanism such as sleeve, sheath or sock.

Balloons and balloon catheters may be particularly useful for the delivery of expandable, implantable medical devices such as stents, grafts, stent-grafts, vena cava filters, hereinafter referred to cumulatively as stents. Stents and catheters used in their delivery are commonly used and as such their structure and function are well known.

Many catheters, including some types of balloon catheters, comprise a proximal portion of a shaft which is often constructed from a variety of non-thermoplastic and/or metallic material(s). This proximal shaft is joined to a distal portion of the catheter at a port area by using a mid-shaft tube that connects the catheter sections together. The port area is the area of the catheter where the proximal guide wire exits the catheter assembly such as is shown in the PRIOR ART drawing labeled FIG. 1. Typically a D-shaped mandrel (not shown) is inserted through the inflation port to support the bonding of the mid-shaft to the sections of the catheter.

A goal of the present invention is to provide a catheter assembly that avoids the necessity of using a D-shaped mandrel through the inflation port. Another goal of the invention is to avoid the use of a mid-shaft tube and bond.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

As indicated above, the present invention may be embodied in a variety of forms. In at least one embodiment the invention is directed to a catheter assembly which avoids the use of a mid-shaft tube by directly engaging the proximal shaft or hypotube directly to the distal outer. Where a guidewire port is required, a portion of the proximal shaft is bonded to the distal outer and a portion is bonded to the inner shaft which defines the proximal guide wire port.

In some embodiments a liner comprised of polyimide and/or other material is engaged to the inner surface of the hypotube and extends distally beyond the weld area between the proximal shaft and distal outer. The liner maintains the inflation lumen during the welding or bonding process without the need of a mandrel. In at least one embodiment the liner is constructed of braided polyimide.

In at least one embodiment the hypotube includes an outer coating of one or more materials such as polyesters; polyurethanes; polyamides; polyolefins including polyethylene and polypropylene; and any copolymers thereof. Some more specific examples of suitable materials include, but are not limited to: nylon; polyester elastomer; polyether/block polyamide, such as Pebax, Hytrel, and/or Arnitel; polyamid such as Grilamid; flouro-polymer, such as Kynar; polyether ether ketone (PEEK); polyethylene (PE); polyurethane; polyolefin copolymer (POC); tetrafluoroethylenes, such as polytetrafluoroethylene (PTFE); etc.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
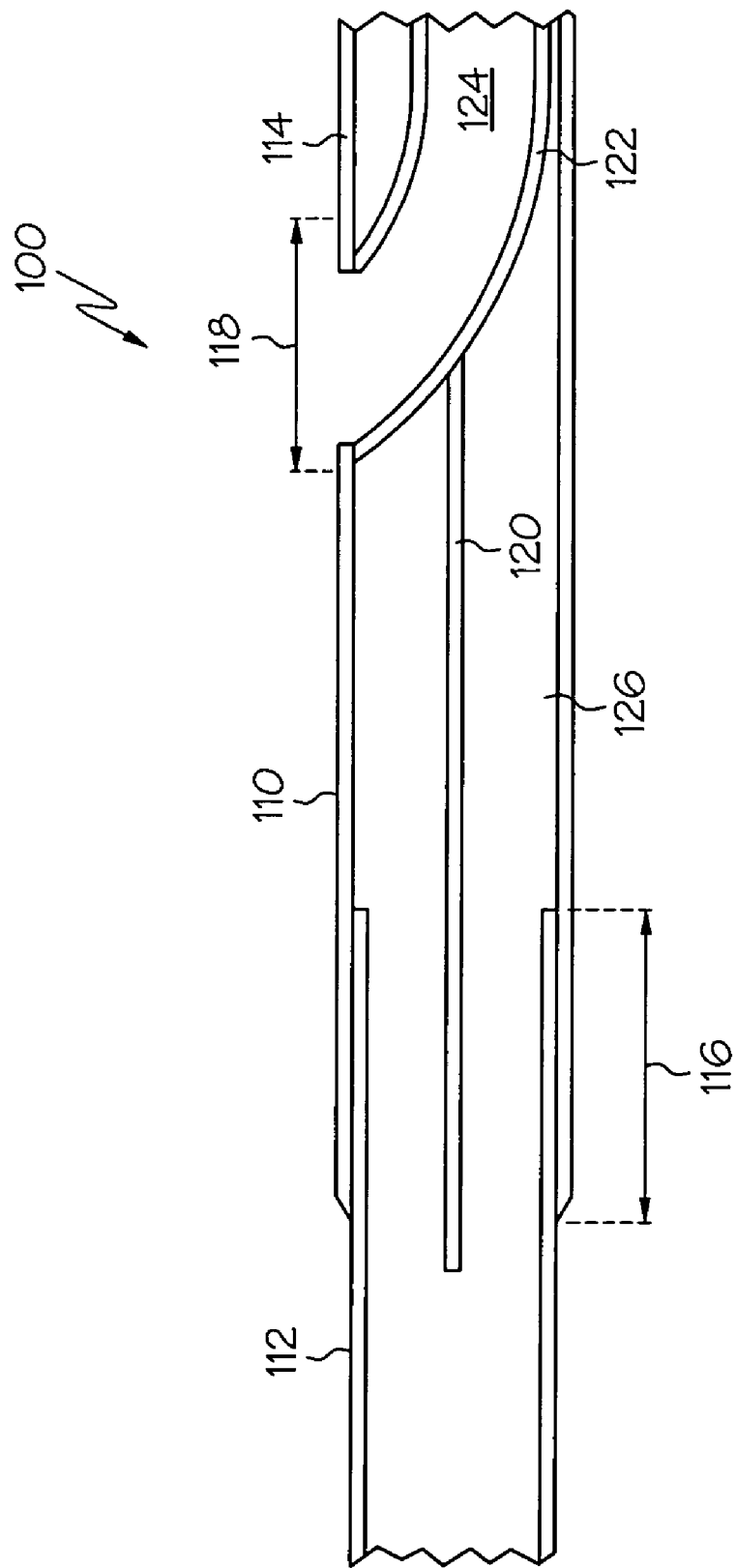
FIG. 1 is a cross-sectional longitudinal side view of a mid-shaft region of a catheter assembly which is representative of a PRIOR ART assembly.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above, FIG. 1 shows a longitudinal cross-section of a PRIOR ART catheter assembly 100, which employs a mid-shaft tube 110 to connect the proximal shaft or hypotube 112 and distal outer 114. The mid-shaft bond 116 is formed where the mid-shaft tube 110 is welded, bonded or otherwise engaged to the proximal shaft 112. A port bond 118 is the region where the mid-shaft tube 110 is bonded to the distal outer 114 and/or the inner shaft 122 which defines a proximal guidewire lumen 124. A core wire 120 extends through the inflation lumen 126 defined by the hypotube 112.

In many prior art assemblies such as the one shown in PRIOR ART FIG. 1, formation of at least the port bond 118 requires the use of a D-shaped mandrel (not shown) which is inserted through the inflation lumen 126 to support the assembly during the bonding or welding process.

Figure 2:
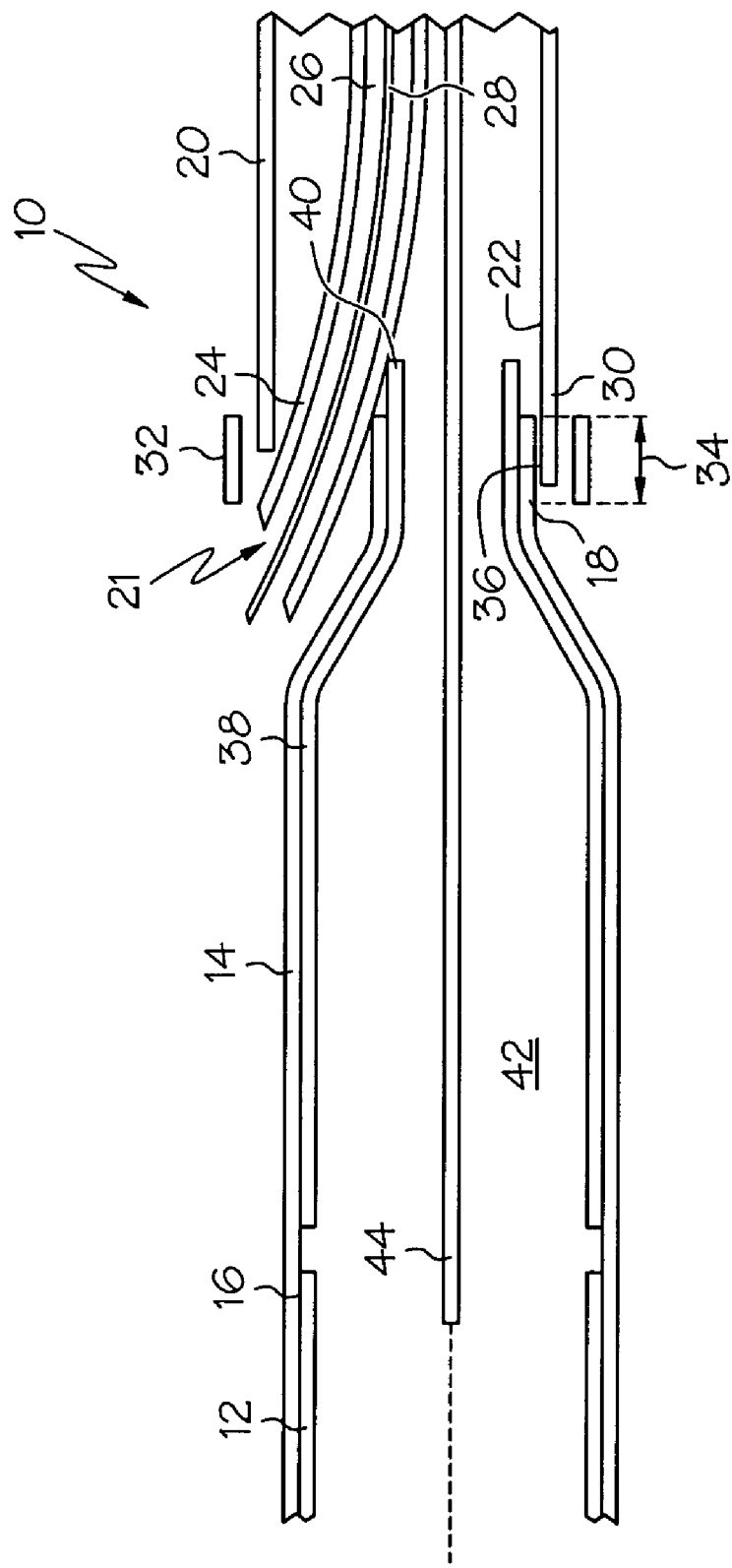
FIG. 2 is a cross-sectional longitudinal side view of an embodiment of the invention.

In at least one embodiment of the present invention a catheter assembly, indicated generally at 10 in FIG. 2, is assembled without employing a mid-shaft tube such as previously described. In some embodiments, catheter 10 is assembled without the need to employ a D-shaped mandrel as well.

In the embodiment shown in FIG. 2 a proximal shaft or hypotube 12 includes a member or coating 14 of one or more materials such as polyesters; polyurethanes; polyamides; polyolefins including polyethylene and polypropylene; and any copolymers thereof. Some more specific examples of suitable materials include, but are not limited to: nylon; polyester elastomer; polyether/block polyamide, such as Pebax, Hytrel, and/or Arnitel; polyamid such as Grilamid; flouropolymer, such as Kynar; polyether ether ketone (PEEK); polyethylene (PE); polyurethane; polyolefin copolymer (POC); tetrafluoroethylenes, such as polytetrafluoroethylene (PTFE); etc.

Coating 14 may be applied to the external surface 16 of at least a portion of the proximal shaft 12, or may be a tubular member of material disposed thereabout. In some embodiments the proximal shaft 12 is at least partially constructed from one or more non-thermoplastic polymers and/or metal. In the embodiment shown, a portion of the coated end region 18 of the proximal shaft 12 is shown engaged to the interior surface 22 of the distal outer shaft 20, in an overlapping configuration. However, alternative configurations such as, an end-to-end (butt-weld) configuration between the outer shaft 20 and the liner 14 and/or proximal shaft 12 may also be used.

Depending on the material selected for coating 14, the coating 14 may act as a lubricious polymer shrinkable tube that is suitable for thermal welding of polymers of the adjacent structures.

In some embodiments the proximal shaft 12 may be constructed of a suitable polymer material to permit direct bonding or other engagement of the proximal shaft 12 to the outer shaft 20 without the need of coating 14. For example, directly the components by thermal weld and ultrasonic fusion are two methods, among others, that may be employed to bond the shaft 20 to the proximal shaft 12.

In the embodiment shown inn FIG. 2, a portion of the end region 18 is also engaged to an inner shaft 24 which defines a lumen 26 through which a proximal guidewire 28 is passed. Where inner shaft 24 also defines the port 29 where the guidewire 28 exits the catheter 10.

Figure 3:
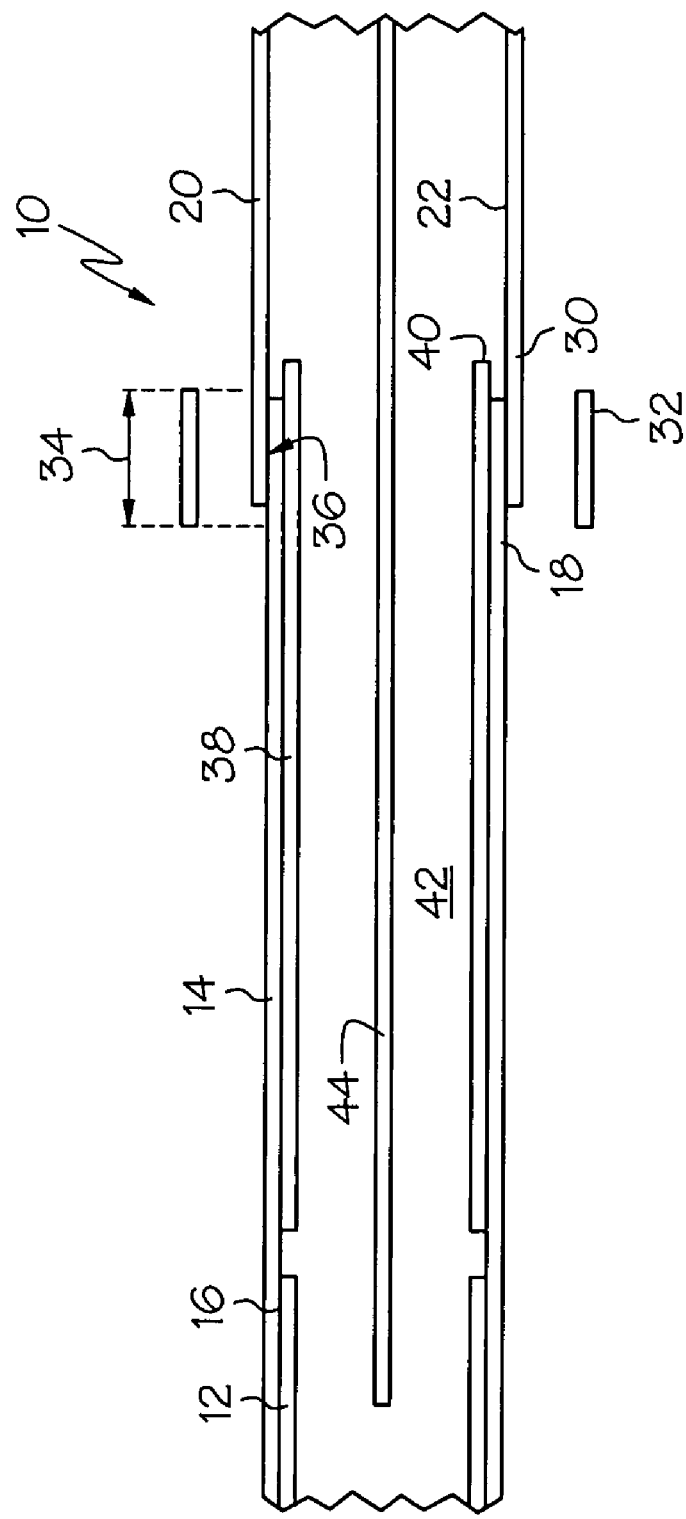
FIG. 3 is a cross-sectional longitudinal side view of an embodiment of the invention.

In some embodiments such as is shown in FIG. 3, the inner shaft and lumen are not included in the construction of the catheter 10. In this embodiment, a coated end region 18 of the proximal shaft 12 is in substantially continuous engagement with the outer shaft 20.

In the embodiments shown in FIGS. 2 and 3 the coated proximal shaft 12 is engaged to the distal outer tube 20 by welding, bonding, physical engagement, or other engagement methods. In at least one embodiment, a heat shrink material 32, such as may be selected from the materials previously mentioned in reference to coating 14, may used to define at least a portion of a bond zone 34 which encompasses the overlapping end regions 18 and 30 of the proximal shaft 12 and outer shaft 20 respectively. When a predetermined amount of heat from a laser, forming jaws, or other device is applied to the bond zone 34, the overlapping end regions 18 and 30 are secured together to form the port bond or seal 36.

In at least one embodiment the length of the overlap of the end regions 18 and 30, or seal 36, is about 1 mm to about 10 mm. In some embodiments the overlap is about 0.5 cm. The length of the bond zone 34, is at least as long as the length of the seal 36, and in at least one embodiment, the bond zone 34 is longer than seal 36. In the embodiment shown in FIG. 2, the bond zone 34 is about 0.6 cm.

In some embodiments, such as are shown in FIGS. 2 and 3, at least the distal end region 18 of the proximal shaft 12 is disposed about an inner layer 38 of polyimide or other material having a melting temperature higher than that of the proximal shaft 12. Layer 38 has sufficient physical characteristics to prevent deformation of the proximal shaft 12 and outer shaft 20 during formation of the seal 36. In at least one embodiment layer 38 is comprised at least partially of braided polyimide. As is best shown in FIG. 2 layer 38 extends distally beyond the end 18 of the proximal shaft 12 to underlay at least a portion of the outer shaft 20. The distally extending portion 40 of layer 38 extends beyond the bond zone 34 to keep the central inflation lumen 42 open during formation of the seal 36. As a result, a core wire 44 is freely moveable through the lumen 42 even after formation of the seal 36.

Figure 4:
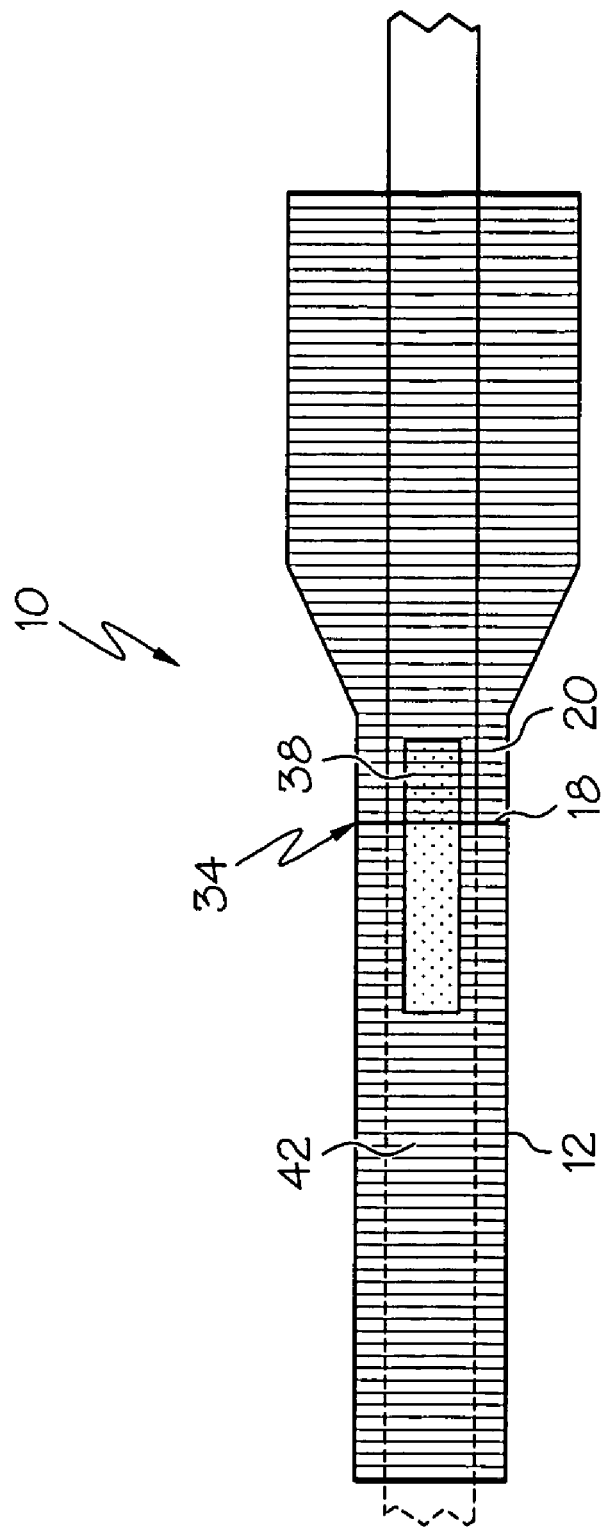
FIG. 4 is a cross-sectional longitudinal side view of an embodiment of the invention.

In at least one embodiment shown in FIG. 4 a catheter assembly 10 comprises a proximal shaft 12. In at least one embodiment, proximal shaft 12 is constructed from at least one polymer material. As shown in FIG. 4, proximal shaft 12 defines an inflation lumen 42. In the embodiment shown the distal outer tube 20 is butt-welded to the end 18 of the proximal shaft 12 at a bond or weld site 34.

An inner layer or tube 38 of polyimide or other material having a melting temperature higher than that of a polymer material of the proximal shaft 12 and outer tube 20 is inserted within the lumen 42 to maintain the lumen during the welding process.

In some embodiments the polyimide tube 38 extends proximally and/or distally beyond the weld site 34. For example in some embodiments the tube 38 may extend about 5 mm or less. Other lengths may be possible. Where the polyimide tube 38 extends beyond the weld site 34, the polyimide tube or member may provide the assembly 10 with improved push and strength characteristics, etc.

Figure 5:
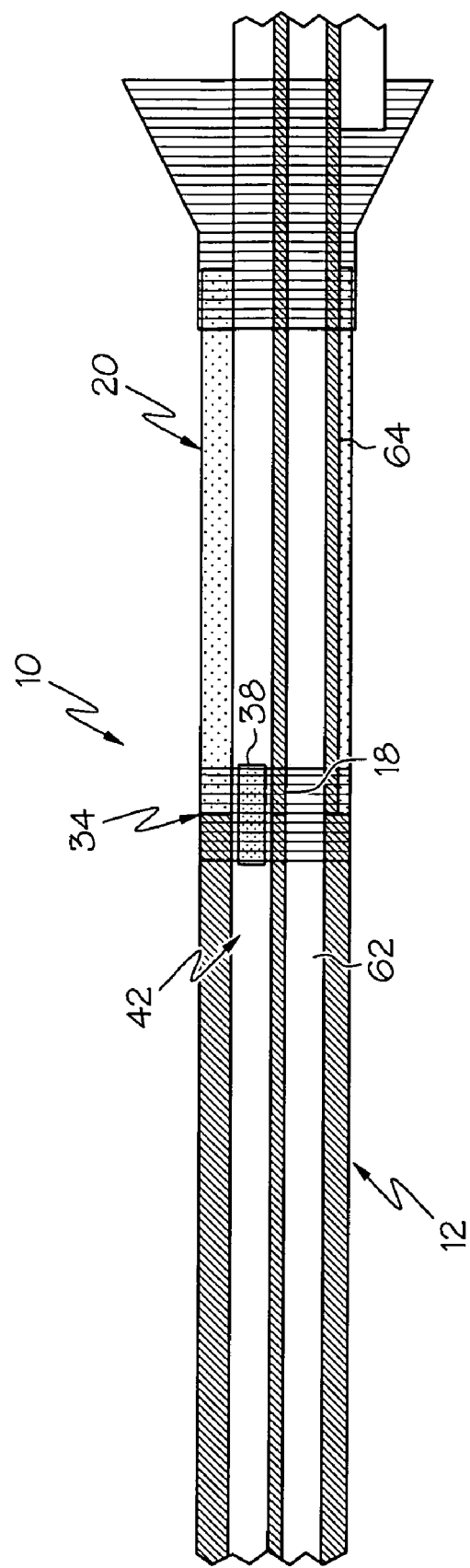
FIG. 5 is a cross-sectional longitudinal side view of an embodiment of the invention.

In at least one embodiment of the invention, such as in the embodiment shown in FIG. 5, shaft 12 may be a bitumen member such as for example may be found on the distal end of a single operator rapid exchange catheter. The shaft 12 defines an inflation lumen 42 and a separate guide wire lumen 62.

In the embodiment shown in FIG. 5 a distal inner shaft or member 64 is butt-welded to the end 18 of the shaft 12 to extend the guide wire lumen distally. The outer tube 20 is positioned about the distal inner member 64 and is also butt-welded at weld site 34 to the end 18 of the shaft 12. The distal outer shaft 20 thus extends the inflation lumen 42 while the inner shaft 64 defines a distal extension of the guide wire lumen 62. In order to facilitate maintenance of the inflation lumen 42 through the weld site 34, a polyimide tube or member 38 is positioned across the weld site 34 within the inflation lumen 42 to maintain the lumen 42 during welding.

As is shown in FIGS. 2 and 3 the use of coated proximal shaft 12 in conjunction with a layer 38 of polyimide, a catheter assembly 10 may be constructed without the need of an external mid-shaft tube and without the need of a mandrel to support the formation of the seal 36. Moreover, as is shown in FIGS. 2 and 3 a catheter formed in accordance with the method described above, requires only a single bond or seal 36 between the proximal shaft 12 and outer shaft 14. This is a significant improvement over prior devices, such as are exemplified in the PRIOR ART device shown in FIG. 1 where a catheter 100 is shown to include two bond sites: the mid-shaft bond 116 and the port bond 118. By eliminating one of the bond sites, a catheter 10, assembled in the manner described above will have lower profile or increased inner lumen diameter, higher burst strength, improved stiffness characteristics, higher tensile strength, improved structural integrity, trackability, and/or be capable of more efficient assembly.

Figure 6:
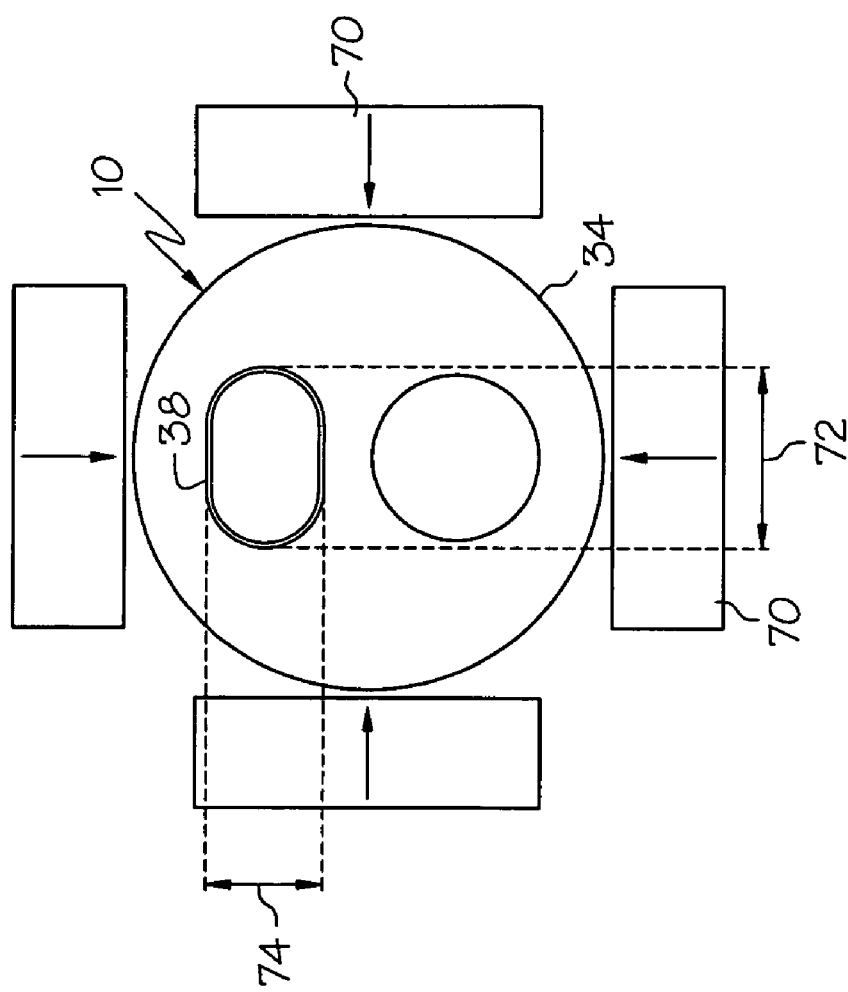
FIG. 6 is a cross-sectional view of an embodiment of the invention being compressed by jaws.

In various embodiments of the invention the use of polyimide layer 38 maintains the inflation lumen during the welding or bonding process without the need of a mandrel. However, in order to ensure formation of a proper weld, as described above, in some embodiments the catheter 10 at bond site 34 is compressed in one or more directions with jaws 70 such as are depicted in FIG. 6. Jaws 70 apply sufficient force to deform the polyimide layer 38 to provide the lumen 42 with a modified shape. In at least one embodiment the modified shape is a substantially elliptical or oval cross-sectional shape such as is shown. In at least one embodiment the lumen 42 will be provided with a width 72 of about 0.019 inches to about 0.03 inches and a height 74 of about 0.012 inches to about 0.025 inches. In at least one embodiment the width 72 of the lumen is about 0.025 inches and the height 74 is about 0.014 inches.

In some embodiments the layer or tubular member 38 of polyimide is as thin as possible. In the embodiment shown in FIG. 6 for example, the layer 38 is less than about 0.003 inches thick. In at least one embodiment the layer 38 is less than about 0.001 inches thick.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A catheter assembly comprising:
   a proximal tubular member, the proximal tubular member having an interior surface and an exterior surface, at least a portion of the exterior surface comprising at least one thermoplastic polymer, the proximal tubular member having a distal end region;
   a distal outer tubular member, the distal outer tubular member having an interior surface, an exterior surface and having a proximal end region, the proximal tubular member and the distal outer tubular member defining at least one continuous central lumen;
   an inner member, the inner member defining a guidewire lumen, the inner member having a proximal end region and a proximal end, the proximal end defining a shaft port, at least a portion of the inner member being positioned external to at least a portion of the exterior surface of the proximal tubular member, at least a portion of the interior surface of the distal outer tubular member being positioned external to at least a portion of the inner member;
   an inner support layer, the inner support layer being attached to the inner surface of the proximal tubular member, a distal end portion of the inner support layer extending distally beyond a distal end of the proximal tubular member; and
   an engagement region, the engagement region having a distal end, a proximal end of the distal outer tubular member being within the engagement region and a distal end of the proximal tubular member being within the engagement region, a first portion of the distal end region of the proximal tubular member being engaged to a portion of the proximal end region of the distal outer tubular member in the engagement region and a second portion of the distal end region of the proximal tubular member being engaged to a portion of the proximal end region of the inner member in the engagement region, the inner support layer extending distally beyond the distal end of the engagement region.

2. The catheter assembly of claim 1 wherein the catheter assembly is a balloon catheter.

3. The catheter assembly of claim 1 wherein the catheter assembly is a monorail catheter or a rapid-exchange catheter.

4. The catheter assembly of claim 1 wherein the proximal tubular member is at least partially constructed from metal.

5. The catheter assembly of claim 1 wherein the proximal tubular member is at least partially constructed from a non-thermoplastic polymer.

6. The catheter assembly of claim 1 wherein the at least one thermoplastic polymer is one or more members of the group consisting of: nylon, polyester elastomer, polyether/block polyamide, polyamide, flouro-polymer, PEEK, PE, polyurethane, POC, PTFE and any combination thereof.

7. The catheter assembly of claim 1 wherein the at least one thermoplastic polymer is a coating.

8. The catheter of claim 1 wherein the proximal tubular member is a hypotube.

9. The catheter of claim 1 wherein the distal outer tubular member is at least partially constructed from at least one member of the group consisting of: nylon, polyester elastomer, polyether/block polyamide, polyamide, flouro-polymer, PEEK, PB, polyurethane, POC, PTFE and any combination thereof.

10. The catheter assembly of claim 1 wherein the interior surface of the at least a portion of the end region of the distal outer tubular member is overlappingly engaged to and about the exterior surface of at least a portion of the end region of the proximal tubular member.

11. The catheter assembly of claim 10 wherein the exterior surface of the at least a portion of the end region of the proximal tubular member comprises the thermoplastic polymer.

12. The catheter assembly of claim 11 wherein the interior surface of the at least a portion of the end region of the distal outer tubular member is heat welded to and about the exterior surface of at least a portion of the end region of the proximal tubular member.

13. The catheter assembly of claim 12 further comprising a heat shrink material, the heat shrink material being disposed about the catheter assembly at the engagement region.

14. The catheter assembly of claim 13 wherein the heat shrink material is longer than the engagement region.

15. The catheter assembly of claim 12 wherein the engagement region is about 1 mm to about 10 mm in length.

16. The catheter assembly of claim 12 wherein the engagement region is at least about 0.6 cm in length.

17. The catheter assembly of claim 11 wherein the interior surface of the at least a portion of the end region of the distal outer tubular member is chemically welded to and about the exterior surface of at least a portion of the end region of the proximal tubular member.

18. The catheter assembly of claim 11 wherein the interior surface of the at least a portion of the end region of the distal outer tubular member is mechanically engaged to and about the exterior surface of at least a portion of the end region of the proximal tubular member.

19. The catheter assembly of claim 1 further comprising a core wire, the core wire being moveable within the at least one continuous central lumen.

20. The catheter assembly of claim 1, the interior surface of the portion of the proximal end region of the distal outer tubular member being engaged to at least a portion of the inner member and the exterior surface of the second portion of the distal end region of the proximal tubular member being engaged to the portion of the proximal end region of the inner member.

21. The catheter assembly of claim 20 wherein the inner member is at least partially constructed from at least one member of the group consisting of: nylon, polyester elastomer, polyether/block polyamide, polyamide, flouro-polymer, PEEK, PB, polyurethane, POC, PTFE and any combination thereof.

22. The catheter assembly of claim 1 wherein the inner support layer is at least partially constructed of a polyimide.

23. The catheter assembly of claim 22 wherein at least a portion of the inner support layer is braided polyimide.

24. The catheter assembly of claim 1 wherein the inner support layer is a tubular member of polyimide material.

25. The catheter assembly of claim 24 wherein the tubular member defines the at least one continuous lumen at the engagement region.

26. The catheter assembly of claim 25 wherein the tubular member has a substantially ovoid cross-sectional shape.

27. The catheter assembly of claim 26 wherein the at least one continuous lumen at the engagement region defined by the tubular member comprises a height and a width, the height being about 0.0 12 inches to about 0.025 inches.

28. The catheter assembly of claim 27 wherein the width is about 0.019 inches to about 0.03 inches.

29. The catheter assembly of claim 28 wherein the height is about 0.014 inches and the width is about 0.025 inches.

30. The catheter assembly of claim 24 wherein the tubular member has a thickness, the thickness being less than about 0.003 inches.

31. The catheter assembly of claim 24 wherein the tubular member has a thickness, the thickness being less than about 0.001 inches thick.

32. A method for assembling a catheter comprising the steps of:
positioning at least a portion of an inner support member within at least a portion of a proximal tubular member;
positioning a first end region of a distal outer tubular member about a first end region of the proximal tubular member so that the first end region of the proximal tubular member is disposed within a lumen defined by the distal outer tubular member, the lumen defined by the proximal tubular member and the lumen defined by the distal outer tubular member defining at least one continuous central lumen,
positioning an inner shaft so that at least a portion of the inner shaft is disposed within at least a portion of the lumen defined by the distal outer tubular member and so that the at least a portion of the inner shaft is disposed between the distal outer tubular member and the first end region of the proximal tubular member, the inner shaft defining a guidewire lumen, a proximal end of the inner shaft defining a port through which a guidewire extends into the inner shaft;
engaging the inner support member to at least a portion of an interior surface of the proximal tubular member;
forming an engagement region, in the engagement region the first end region of the proximal tubular member is engaged to the a portion of the distal outer tubular member and the proximal tubular member is engaged to a portion of the inner shaft , a proximal end of the distal outer tubular member and a distal end of the proximal tubular member being within the engagement region, and the inner support member extending distally beyond the distal end of the proximal tubular member and distally beyond an distal end of the engagement region.

33. The method of claim 32 the first end region of the proximal tubular member being engaged to the portion of the distal outer tubular member by applying energy to at least the engagement region, the energy being sufficient to cause at least a portion of the first end region of the proximal tubular member and at least a portion of the distal end of the distal outer tubular member to at least partially melt, the energy being insufficient to melt the inner support layer.

34. The method of claim 33 further comprising the step of applying a compressive force in at least one direction to at least the engagement region.

35. The method of claim 34 wherein the compressive force provides the inner support layer with a substantially ovoid cross-sectional shape.

* * * * *